United States Patent
Bumbalough

(10) Patent No.: US 6,267,746 B1
(45) Date of Patent: *Jul. 31, 2001

(54) MULTI-DIRECTIONAL STEERABLE CATHETERS AND CONTROL HANDLES

(75) Inventor: Timothy Ray Bumbalough, Fullerton, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/274,050

(22) Filed: Mar. 22, 1999

(51) Int. Cl.$^7$ .................................................. A61M 37/00
(52) U.S. Cl. ........................................................ 604/95.01
(58) Field of Search .............................. 604/95.01–95.05; 600/139–152

(56) References Cited

U.S. PATENT DOCUMENTS

| | | | |
|---|---|---|---|
| Re. 34,502 | 1/1994 | Webster, Jr. | 607/125 |
| 4,976,688 | 12/1990 | Rosenblum | 604/95 |
| 5,228,441 | 7/1993 | Lundquist | 128/642 |
| 5,656,030 | 8/1997 | Hunjan et al. | 604/95 |
| 5,865,800 | * 2/1999 | Mirarchi et al. | 604/95 |
| 5,906,590 | * 5/1999 | Hunjan et al. | 604/95 |

\* cited by examiner

Primary Examiner—Sharon Kennedy
Assistant Examiner—Ann Y Lam
(74) Attorney, Agent, or Firm—Christie, Parker & Hale, LLP

(57) ABSTRACT

A steerable catheter comprises a catheter body, a tip section mounted to the distal end of the catheter body, and a control handle mounted to the proximal end of the catheter body. The control handle comprises a housing having a piston chamber and a piston slidably mounted in the piston chamber. The piston is longitudinally movable between proximal and distal positions. A longitudinal groove having proximal and distal ends and extends along a portion of the length of the piston. A puller wire anchor is slidably disposed within the longitudinal groove. A puller wire extends from the control handle, through a lumen in the catheter body and into a lumen in the tip section. The proximal end of the puller wire is fixedly attached to the puller wire anchor. A set screw is fixedly attached to the handle housing and extends radially inwardly into the longitudinal groove in the piston. When the piston is slid distally relative to the handle housing, the set screw prevents the puller wire anchor from moving distally with the piston, resulting in deflection of the tip section in the direction of the side to which the puller wire is anchored.

18 Claims, 12 Drawing Sheets

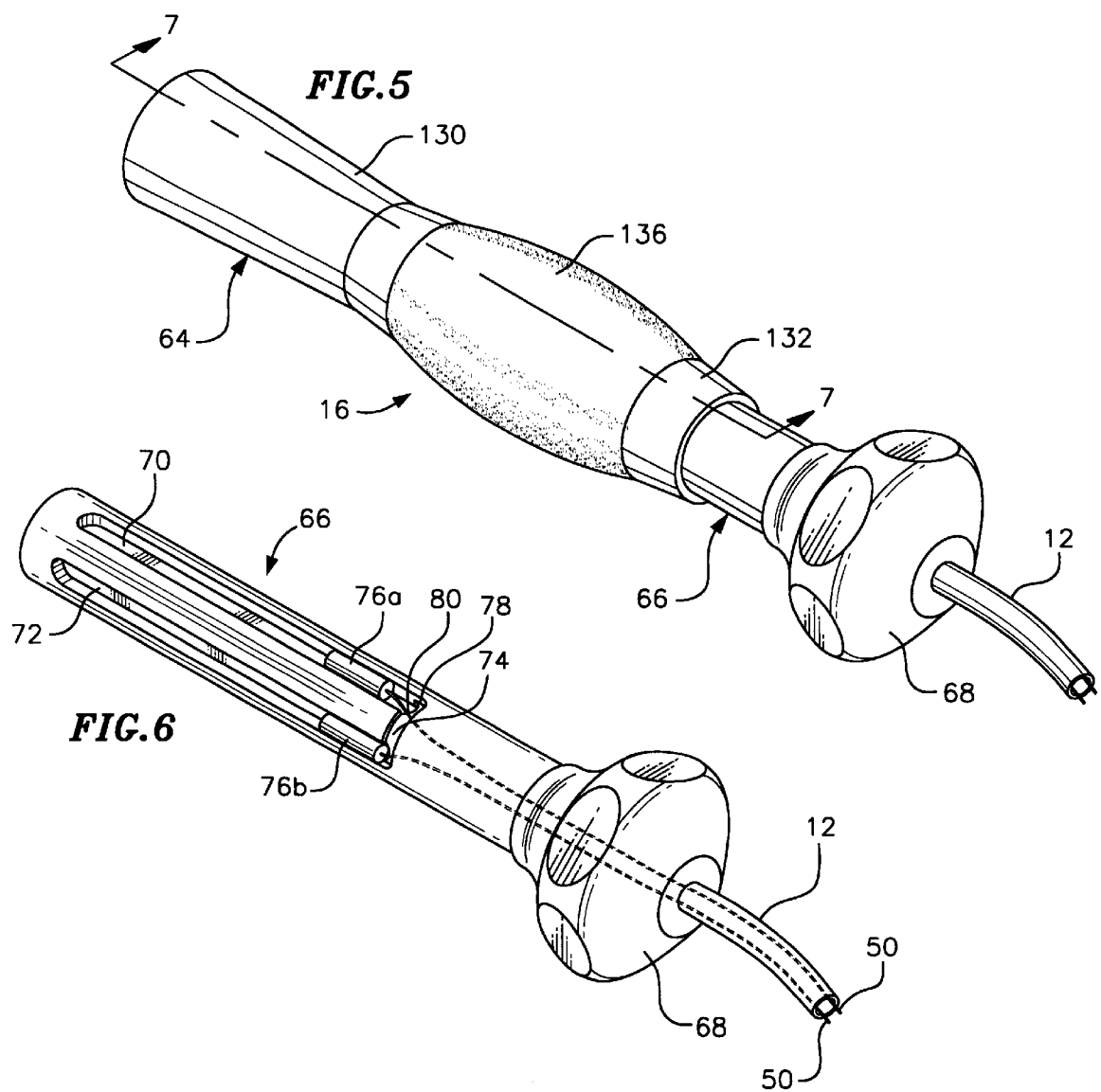

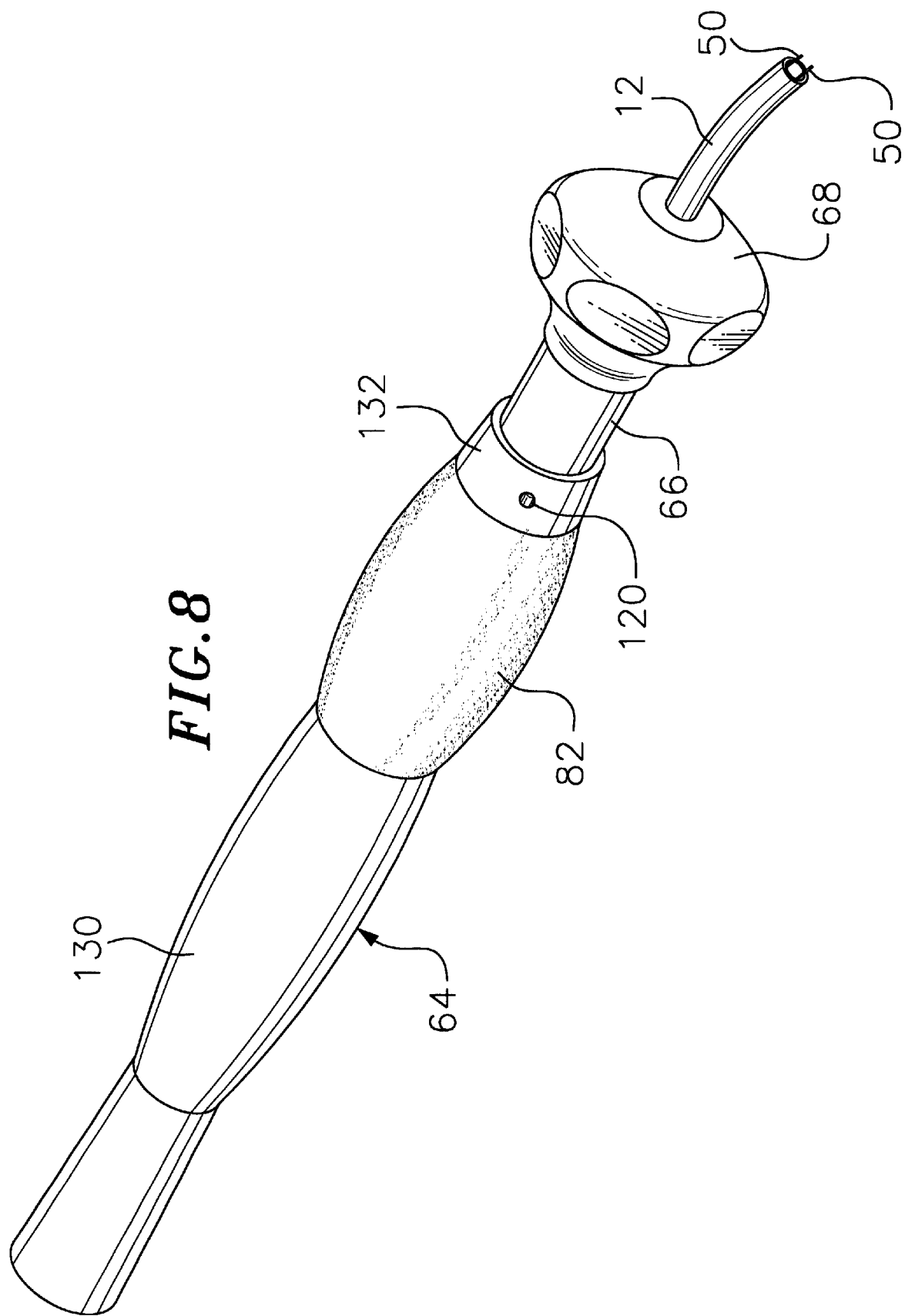

US 6,267,746 B1

MULTI-DIRECTIONAL STEERABLE CATHETERS AND CONTROL HANDLES

FIELD OF THE INVENTION

The present invention is directed to multidirectional steerable catheters and to multidirectional control handles for use with the multidirectional steerable catheters.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Steerable catheters are generally well-known. For example, U.S. Pat. No. RE 34,502 describes a catheter having a control handle comprising a housing having a piston chamber at its distal end. A piston is mounted in the piston chamber and is afforded lengthwise movement. The proximal end of the elongated catheter body is attached to the piston. A puller wire is attached to the housing and extends through the piston, through the catheter body, and into a tip section at the distal end of the catheter body. The distal end of the puller wire is anchored in the tip section of the catheter. In this arrangement, lengthwise movement of the piston relative to the housing results in deflection of the catheter tip section.

The design described in U.S. Pat. No. RE 34,502 is generally limited to a catheter having a single puller wire. If a bidirectional catheter is desired, i.e., a catheter that can be deflected to form two different curves (e.g., deflect in more than one direction), more than one puller wire becomes necessary. When two puller wires are used, however, it is undesirable for both wires to be moved simultaneously. The handle design disclosed in U.S. Pat. No. RE 34,502 is not suitable for a two puller wire system. Accordingly, a need exists for a control handle capable of independently moving each of two puller wires but preventing simultaneous movement of the puller wires.

SUMMARY OF THE INVENTION

The present invention is directed to steerable catheters and novel control handles for use therewith. The catheter comprises a catheter body having a tubular wall, proximal and distal ends, and at least one lumen extending therethrough. A tip section comprising flexible tubing having proximal and distal ends and at least one lumen extending therethrough is fixedly attached at its proximal end to the distal end of the catheter body.

A control handle is mounted at its distal end to the proximal end of the catheter body. The control handle comprises a housing having proximal and distal ends and a piston chamber and a piston having proximal and distal ends slidably mounted in the piston chamber of the housing. The distal end of the piston is fixedly attached to the proximal end of the catheter body. The piston is longitudinally movable between proximal and distal positions. A longitudinal groove having proximal and distal ends extends along a portion of the length of the piston. A puller wire anchor is slidably disposed within the longitudinal groove. A puller wire having proximal and distal ends extends from the control handle, through a lumen in the catheter body and into a lumen in the tip section. The proximal end of the puller wire is fixedly attached to the puller wire anchor in the control handle.

Means are provided for selectively causing deflection of the tip section in a select direction in response to proximal movement of the puller wire anchor relative to the catheter body. In one embodiment, the deflecting means comprises an off-axis lumen through which the puller wire extends and an anchor that anchors the puller wire to the side or distal end of the tip section or means for anchoring the puller wire to a tip electrode mounted at the distal end of the tip section. Another deflecting means is described in U.S. Pat. Nos. 5,336,182 and 5,364,351, the disclosures of which are incorporated herein by reference.

Means are also provided for blocking, preferably releasably blocking, distal movement of the puller wire anchor within the groove when the piston is moved distally. Preferably the prevention means comprises a set screw fixedly attached to the handle housing that extends radially inwardly into the longitudinal groove in the piston. When the piston is slid distally relative to the handle housing, the set screw prevents the puller wire anchor from moving distally with the piston.

In another embodiment, there is provided a multidirectional steerable catheter. The catheter comprises a catheter body having a tubular wall, proximal and distal ends, and at least one lumen extending therethrough. A tip section comprising flexible tubing having proximal and distal ends and at least one lumen extending therethrough it fixedly attached at its proximal end to the distal end of the catheter body.

A control handle is mounted at its distal end to the proximal end of the catheter body. The control handle comprises a housing having proximal and distal ends and a piston chamber. A piston is slidably and rotatably mounted in the piston chamber of the housing. The distal end of the piston is fixedly attached to the proximal end of the catheter body. The piston is longitudinally movable between proximal and distal positions and rotatably movable between first and second positions.

Two longitudinal grooves having proximal and distal ends extends along a portion of the length of the piston. First and second puller wire anchors are each slidably disposed within a corresponding longitudinal groove. A circumferential groove preferably connects the distal ends of the longitudinal grooves. First and second puller wires having proximal and distal ends each extend from the control handle, through a lumen in the catheter body and into a lumen in the tip section. The proximal end of each puller wire is fixedly attached to a separate the puller wire anchor in the control handle.

A first means for causing deflection of the tip section to form a first curve in response to proximal movement of the first puller wire relative to the catheter body is provided. A second means for causing deflection of the tip section to form a second curve different from the first curve in response to proximal movement of the second puller wire relative to the catheter body is also provided. The first and second deflecting means can be any suitable means, such as those described above. Also provided is a means for selectively preventing distal movement of one of the first and second puller wire anchors when the piston is moved distally. A preferred means for selectively preventing distal movement of one of the first and second puller wire anchors comprises a set screw that extends radially inwardly from the handle housing into the circumferential groove. The piston can be rotated between first and second positions relative to the housing, resulting in movement of the circumferential groove relative to the set screw. When the piston is in its first position, the set screw is aligned with the first longitudinal groove, and, as the piston is moved distally relative to the handle housing, the set screw prevents distal movement of the puller wire anchor in the first longitudinal groove. Similarly, when the piston is in its second position, the set screw is aligned with the second longitudinal groove, and, as the piston is moved distally relative to the handle housing, the set screw prevents distal movement of the puller wire anchor in the second longitudinal groove.

By this design, the tip section can be deflected to form two different curves, and preferably be deflected in two opposite directions. However, simultaneous movement of the puller wires may be prevented by the releasable preventing means.

DESCRIPTION OF THE DRAWINGS

These and other features and advantages of the present invention will be better understood by reference to the following detailed description when considered in conjunction with the accompanying drawings wherein:

FIG. 5 is a perspective view of a control handle according to the invention.

FIG. 6 is a perspective view of the piston of the control handle of FIG. 5.

FIG. 8 is a perspective view of an alternative embodiment of a control handle according to the invention.

DETAILED DESCRIPTION

In a particularly preferred embodiment of the invention there is provided a bidirectional steerable catheter 10. As shown in FIGS. 1 to 4, the catheter comprises an elongated catheter body 12 having proximal and distal ends, a tip section 14 at the distal end of the catheter body, and a control handle 16 at the proximal end of the catheter body.

Figure 1:
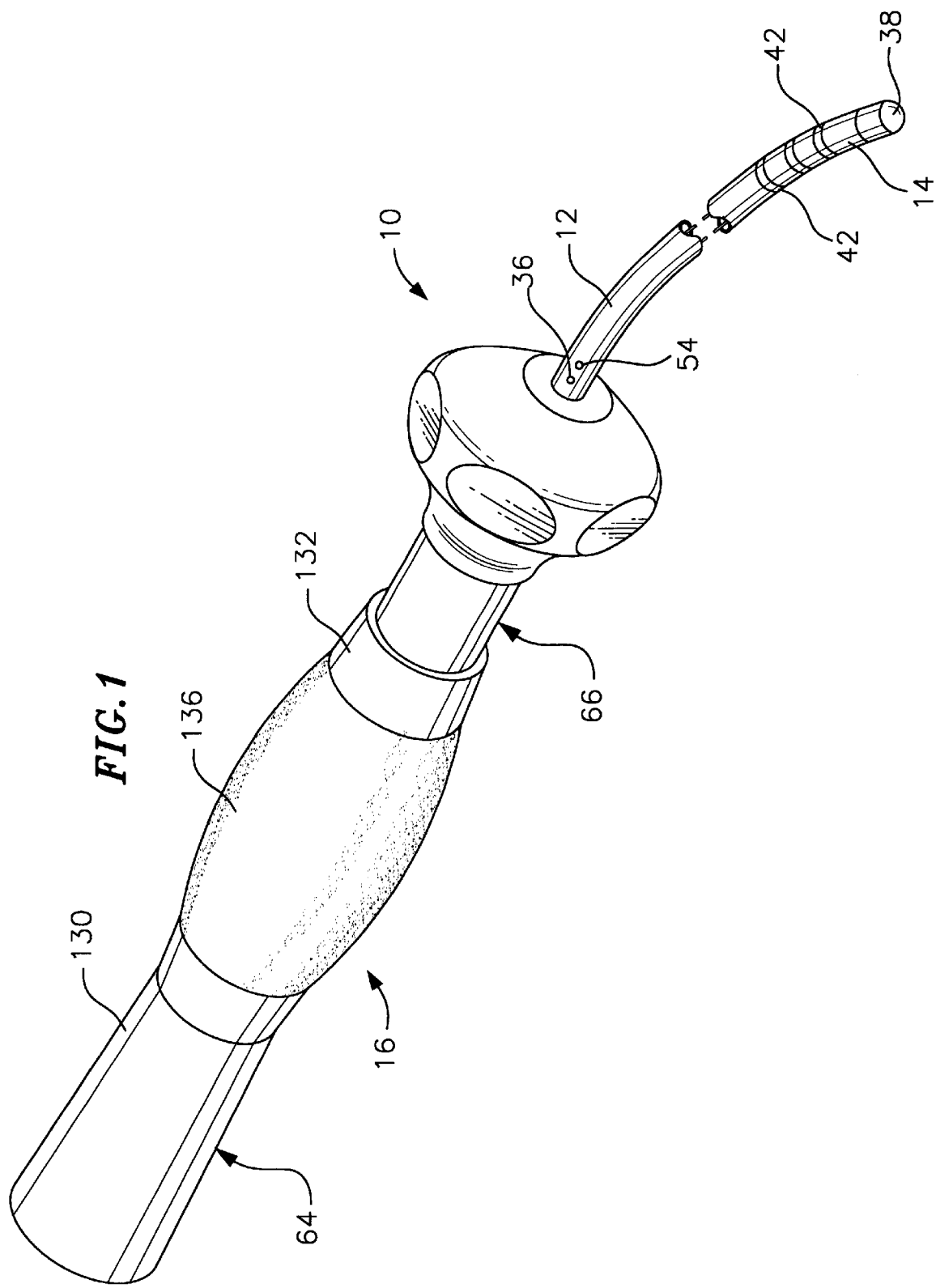
FIG. 1 is a perspective view of a catheter according to the invention.
Figure 2:
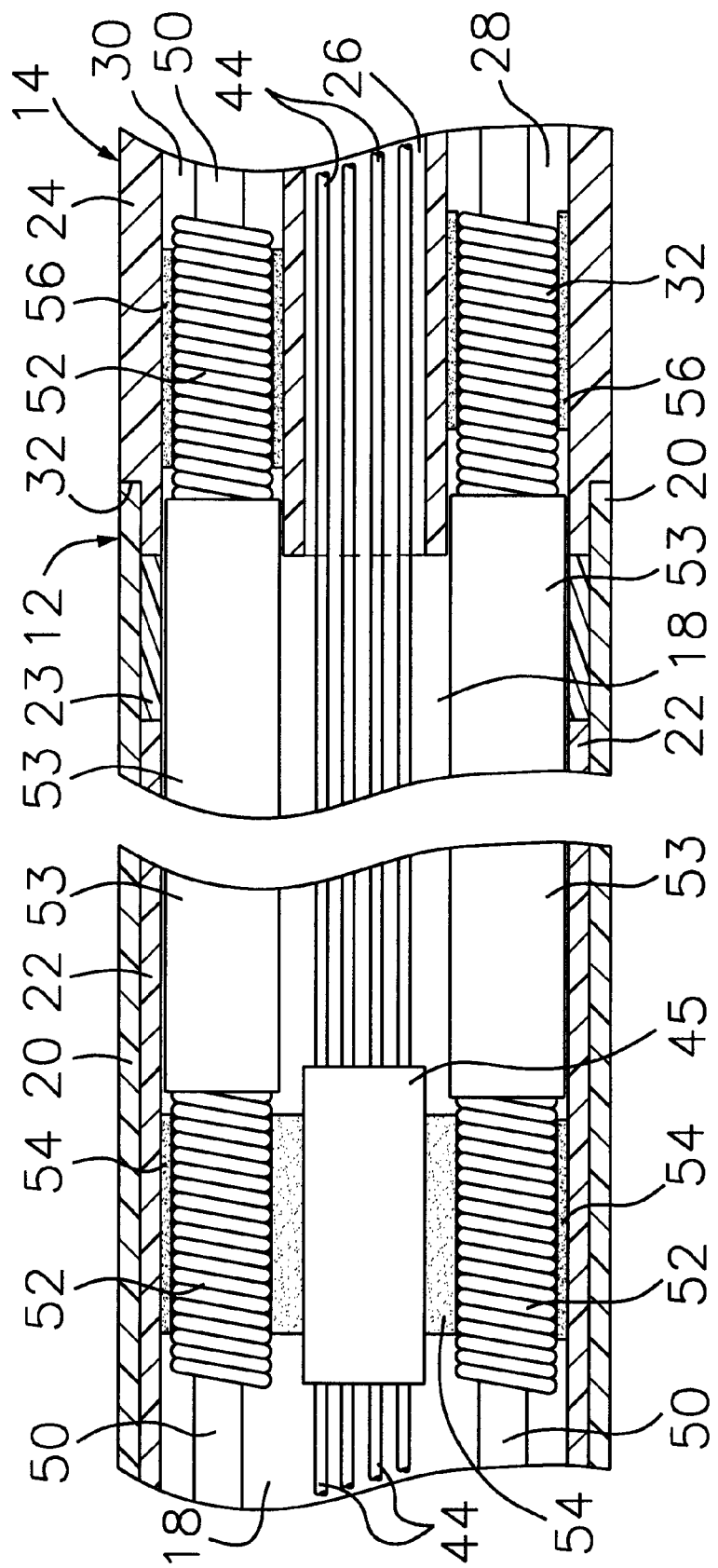
FIG. 2 is a side cross-sectional view of the catheter body and tip section of a catheter according to the invention.

With reference to FIGS. 1 and 2, the catheter body 12 comprises an elongated tubular construction having a single, axial or central lumen 18. The catheter body 12 can have additional lumens if desired, although a single central lumen 18 is presently preferred. The catheter body is flexible, i.e., bendable, but substantially non-compressible along its length. The catheter body 12 can be of any suitable construction and made of any suitable material. A presently preferred construction comprises an outer wall 20 made of polyurethane or PEBAX™. The outer wall 20 comprises an imbedded braided mesh of stainless steel or the like to increase torsional stiffness of the catheter body 12 so that, when the control handle 16 is rotated, the tip section 14 will rotate in a corresponding manner.

The outer diameter of the catheter body 12 is not critical, but is preferably no more than about 8 french, more preferably about 7 french. Likewise, the thickness of the outer wall 20 is not critical, but is thin enough so that the central lumen 18 can accommodate at least two puller wires and one or more electrode lead wires. The inner surface of the outer wall 20 is lined with a stiffening tube 22, which can be made of any suitable material, such as polyimide or nylon. The stiffening tube 22, along with the braided outer wall 20, provides improved torsional stability while at the same time minimizing the wall thickness of the catheter, thus maximizing the diameter of the central lumen 18. The outer diameter of the stiffening tube 22 is about the same as or slightly smaller than the inner diameter of the outer wall 20.

Figure 3:
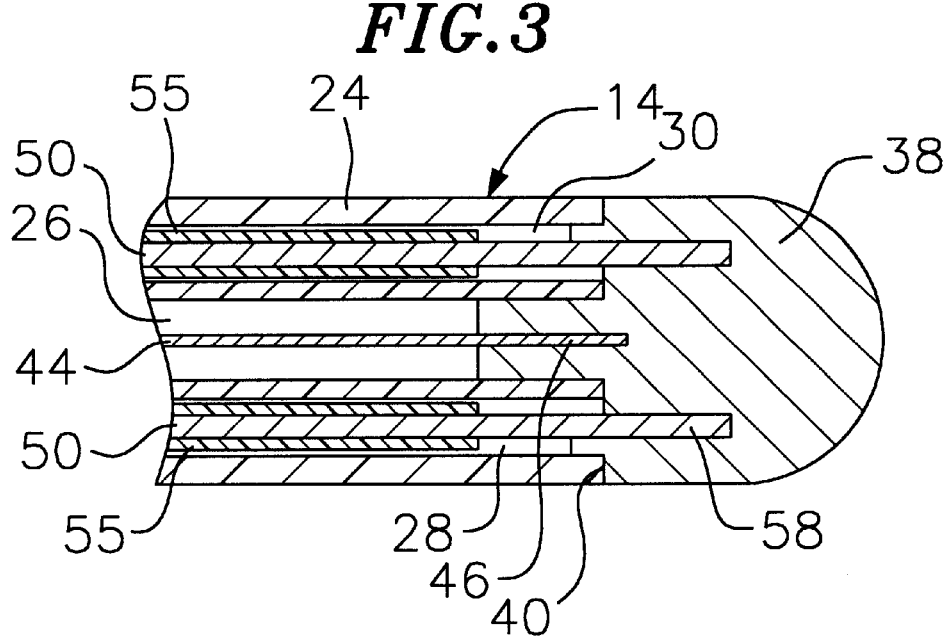
FIG. 3 is a side cross-sectional view of the tip section of a catheter according to the invention.

As shown in FIGS. 2 and 3, the tip section 14 comprises a short section of tubing 24 having an axial lumen 26 and first and second off-axis lumens 28 and 30. The tubing 24 is made of a suitable non-toxic material that is preferably more flexible than the catheter body 12. A presently preferred material for the tubing 24 is braided polyurethane, i.e., polyurethane with an embedded mesh of braided stainless steel or the like. The outer diameter of the tip section 14, like that of the catheter body 12, is preferably no greater than about 8 french, more preferably about 7 french. Alternatively, the tip section 14 can have only two lumens, both off-axis lumens. A description of such a design is provided in U.S. patent application Ser. No. 09/205,631, entitled "Bidirectional Electrode Catheter", the disclosure of which is incorporated herein by reference.

A preferred means for attaching the catheter body 12 to the tip section 14 is illustrated in FIG. 2. The proximal end of the tip section 14 comprises an outer circumferential notch 32 that receives the inner surface of the outer wall 20 of the catheter body 12. The tip section 14 and catheter body 12 are attached by glue or the like. Before the tip section 14 and catheter body 12 are attached, the stiffening tube 22 is inserted into the catheter body. The distal end of the stiffening tube 22 is fixedly attached near the distal end of the catheter body 12 by forming a glue joint (not shown) with polyurethane glue or the like. Preferably a small distance, e.g., about 3 mm, is provided between the distal end of the catheter body 12 and the distal end of the stiffening tube 22 to permit room for the catheter body 12 to receive the notch 32 of the tip section 14. A force is applied to the proximal end of the stiffening tube 22, and, when the stiffening tube is under compression, a first glue joint (not shown) is made between the stiffening tube 22 and the outer wall 20 by a fast drying glue joint, e.g., Super Glue™. Thereafter a second glue joint (not shown) is formed between the proximal ends of the stiffening tube 22 and outer wall 20 using a slower drying but stronger glue, e.g., polyurethane.

If desired, a spacer 23 can be located within the catheter body between the distal end of the stiffening tube and the proximal end of the tip section. The spacer 23 provides a transition in flexibility at the junction of the catheter body and tip section, which allows this junction to bend smoothly without folding or kinking. A catheter having such a spacer is described in U.S. patent application Ser. No. 5,964,757, entitled "Steerable Direct Myocardial Revascularization Catheter", the disclosure of which is incorporated herein by reference.

At the distal end of the tip section 14 is a tip electrode 38. Preferably the tip electrode 38 has a diameter about the same as the outer diameter of the tubing 24. The tip electrode 38 is attached to the tubing 24 by creating a notch 40 in the proximal end of the tip electrode, placing the proximal end of the tip electrode on the distal end of the tubing, and filling the notch with glue.

In the depicted embodiment, three ring electrodes 42 are mounted on the tubing 24 proximal to the tip electrode 38. Each ring electrode 42 is slid over the tubing 24 and fixed in place by glue or the like. It is understood that the presence, number and position of ring electrodes may vary as desired. Similarly, a tip electrode may be excluded if desired. The tip electrode 38 and ring electrodes 42. Can be made of any suitable material, and are preferably machined from platinum-iridium bar (90% platinum/10% iridium).

The tip electrode 38 and ring electrodes 42 are each connected to a separate electrode lead wire 44. The lead wires 44 extend through the axial lumen 26 of the tip section 14, the central lumen 18 of the catheter body 12, and the control handle 16, and terminate at their proximal end in an input jack (not shown) that may be plugged into an appropriate monitor (not shown). If desired, the portion of the lead wires 44 extending through the central lumen 18 of the catheter body 12, control handle 16 and proximal end of the tip section 14 can be enclosed within a protective sheath (not shown), which can be made of any suitable material, preferably polyimide.

The lead wires 44 are attached to the tip electrode 38 and ring electrodes 42 by any suitable conventional technique. Connection of a lead wire 44 to the tip electrode 38 is accomplished, for example, by welding the lead wire 44 into a hole 46 in the tip electrode.

Connection of a lead wire 44 to a ring electrode 42 is preferably accomplished by first making a small hole through the tubing 24. Such a hole can be created, for example, by inserting a needle through the tubing 24 and heating the needle sufficiently to form a permanent hole (not shown). A lead wire 44 is then drawn through the hole by using a microhook or the like. The ends of the lead wires 44 are then stripped of any coating and soldered or welded to the underside of the ring electrode 42, which is then slid into position over the hole and fixed in place with polyurethane glue or the like.

Two puller wires 50, each having proximal and distal ends, extend through the catheter body 12. The puller wires 50 are anchored at their proximal ends to the control handle 16 and at their distal ends to the tip section 14. The puller wires 50 are made of any suitable metal, such as stainless steel or Nitinol, and are preferably coated with Teflon™ or the like. The coating imparts lubricity to the puller wires 50. The puller wires 50 preferably each have a diameter ranging from about 0.006 inch to about 0.010 inch.

Two compression coils 52 are provided in the catheter body 12, each in surrounding relation to a corresponding puller wire 50. The compression coils 52 extend from the proximal end of the catheter body 12 to the proximal end of the tip section 14. The compression coils 52 are made of any suitable metal, preferably stainless steel. The compression coils 52 are tightly wound on themselves to provide flexibility, i.e., bending, but to resist compression. The inner diameter of each compression coil 52 is preferably slightly larger than the diameter of the corresponding puller wire 50. The Teflon™ coating on the puller wires 50 allows them to slide freely within the compression coils 52. The outer surface of each compression coil 52 is covered by a flexible, non-conductive sheath 53, e.g., made of polyimide tubing, to prevent contact between the compression coils 52 and the lead wires 44.

Each compression coil 52 is anchored at its proximal end to the proximal end of the stiffening tube 22 in the catheter body 12 by glue joint 54 and at its distal end to the tip section 14 by glue joint 56. Both glue joints 54 and 56 preferably comprise polyurethane glue or the like. The glue may be applied through a hole (not shown) made between the outer surface of the catheter body 12 and the central lumen 18. Such a hole may be formed, for example, by a needle or the like that punctures the outer wall 20 of the catheter body 12 and the stiffening tube 22, which is heated sufficiently to form a permanent hole. The glue is then introduced through the hole to the outer surface of the compression coil 52 and wicks around the outer circumference to form a glue joint about the entire circumference of the compress coil. A short section of plastic tubing 45 is provided around the lead wires 44 near the glue joint 54 to provide the lead wires with flexibility within the glue joint. Alternatively, the distal ends of the compression coils 52 can be anchored in the distal end of the catheter body 12.

In the depicted embodiment, the puller wires 50 extend into the first off-axis lumen 28 and second off-axis lumen 30 of the tip section 14. Each puller wire 50 extends through a plastic, preferably Teflon™, sheath 55, which prevents that puller wire from cutting into the wall of the tip section 14 when the tip section is deflected. Each puller wire 50 is anchored at its distal end to the tip electrode 38 within a blind hole 58. Preferably the puller wires 50 are anchored in opposite sides of the tip electrode 38 so that the tip section can deflect in two opposing directions, as described in more detail below. A preferred method for anchoring each puller wire 50 in the tip electrode 38 is by crimping metal tubing (not shown) to the distal end of each puller wire 50 and soldering the metal tubing inside the blind hole 58. Other means known to those skilled in the art for anchoring the puller wires 50 in the tip electrode 38 could also be used.

Figure 4:
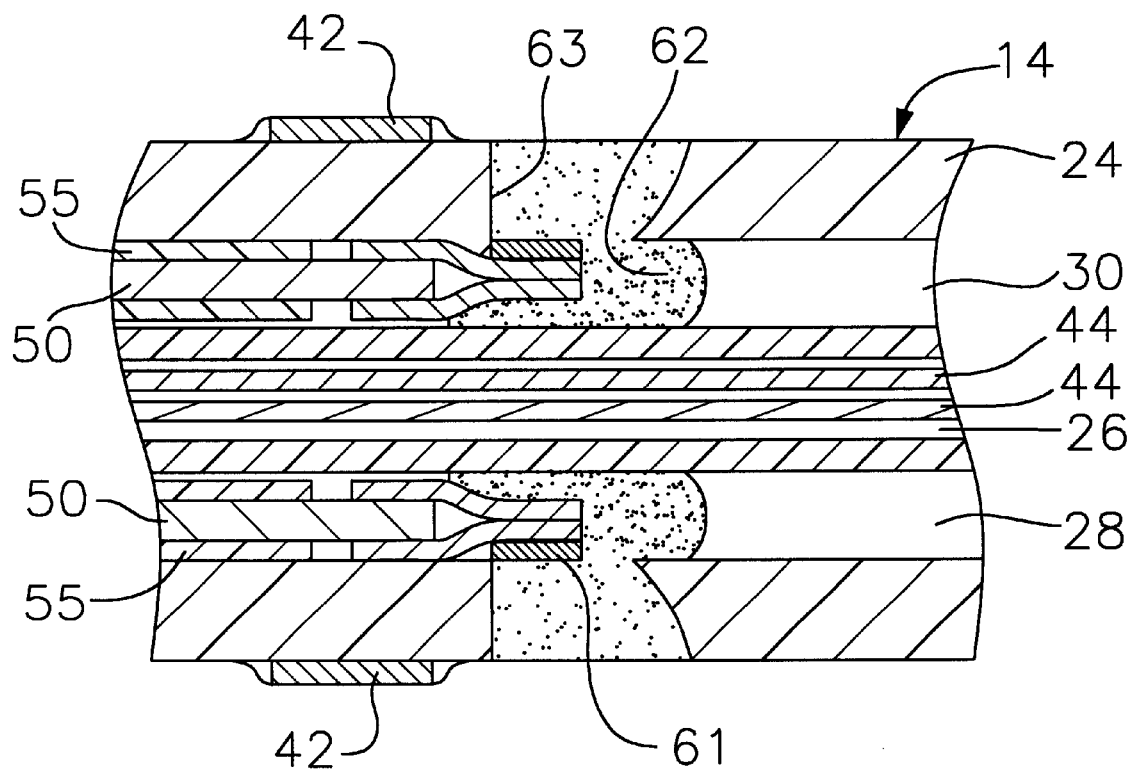
FIG. 4 is a side cross-sectional view of a portion of the tip section showing one means for anchoring the puller wires to the sides of the tip section.

Alternatively, one or both of the puller wires 50 can be anchored to the sides of the tip section 14. The distal ends of the puller wires 50 comprise T-bar anchors 61 as described above and are preferably anchored by glue 62 in notches 63 in the side wall of the flexible tubing 24 as shown in FIG. 4 and as described in U.S. Pat. No. 6,064,908, the desclosure of which is incorporated herein by reference.

If desired, the puller wires 50 can both be anchored to the same side of the tip section with one puller wire anchored proximal the other puller wire. With this design, the tip section could form a U-shaped curve. Other puller wire anchoring arrangements could also be provided to permit the tip section to deflect to form two different curves.

Figure 7:
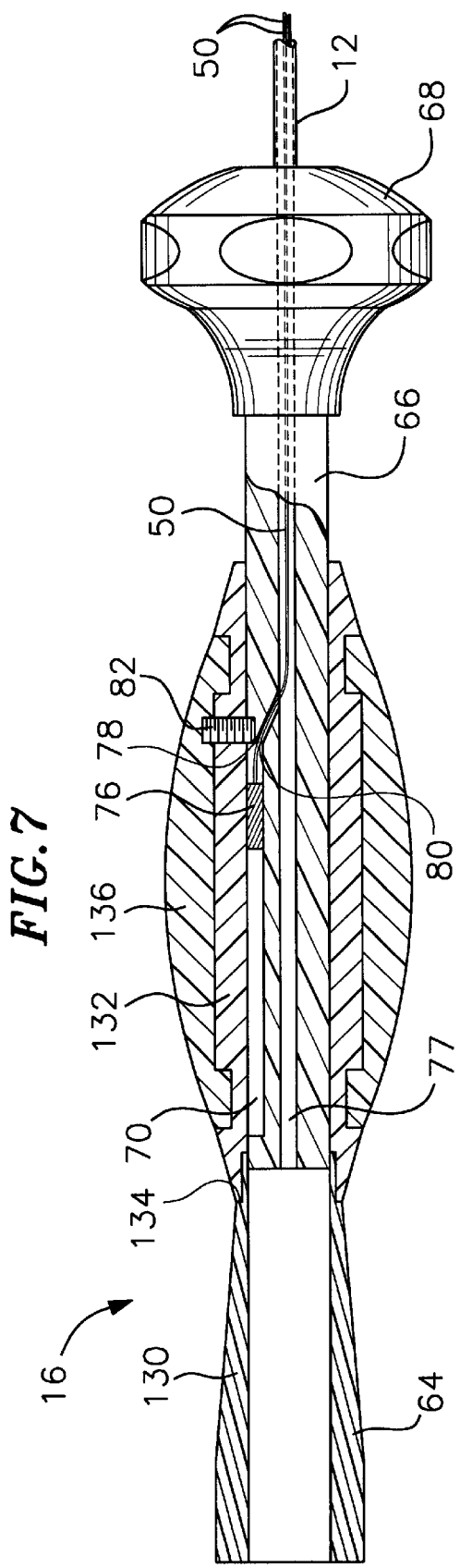
FIG. 7 is a side partial cross-sectional view of the control handle of FIG. 5 along line 7—7.
Figure 9A:
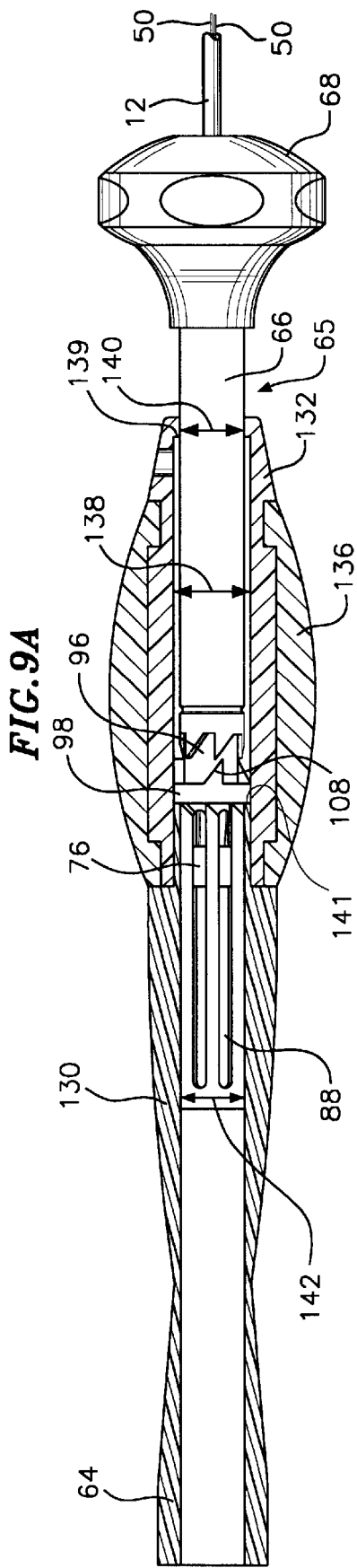
FIG. 9A is a side cross partial cross-sectional view of the handle of FIG. 8 without the sleeve wherein only the handle housing is shown in cross section.
Figure 9B:
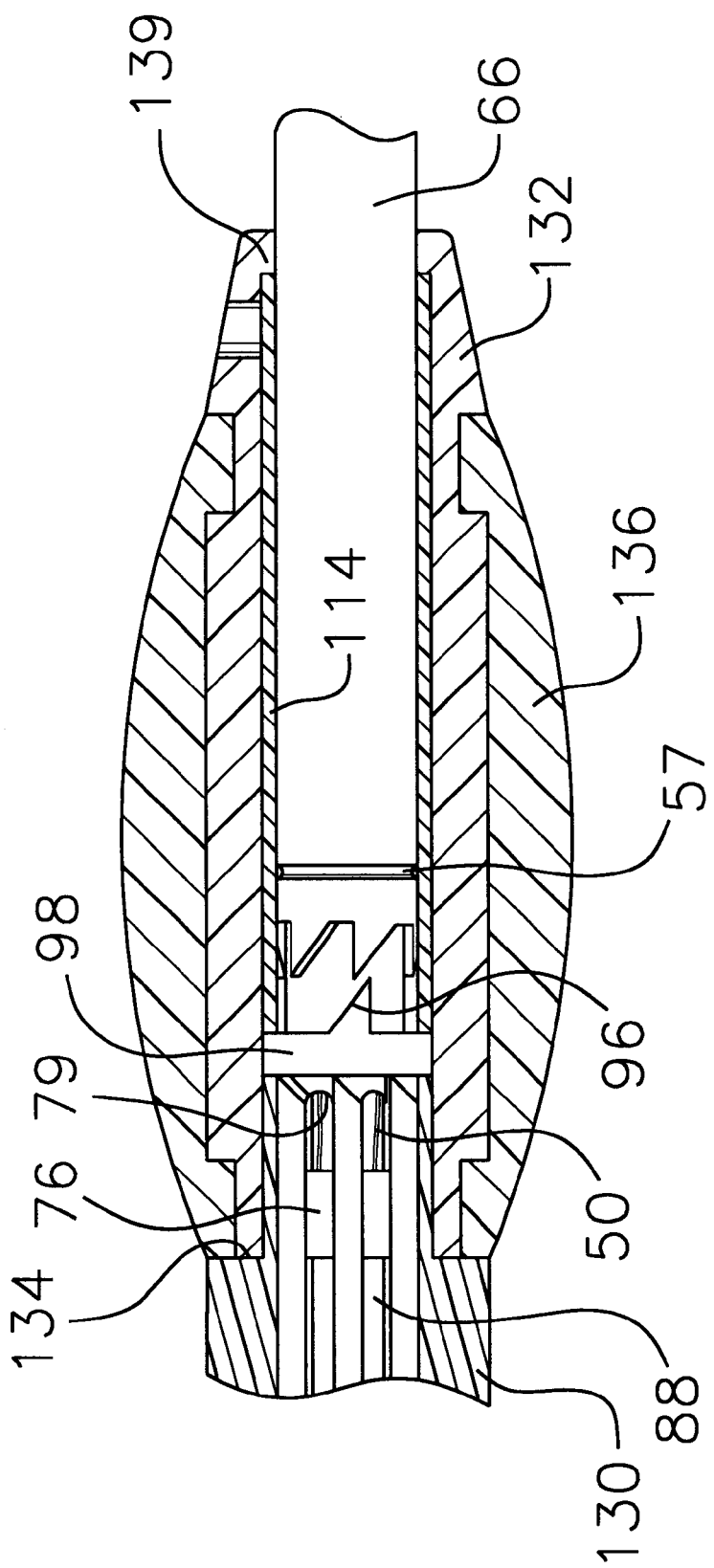
FIG. 9B is a close-up side cross partial cross-sectional view of the handle of FIG. 9 with the sleeve.

The control handle 16, illustrated in FIGS. 5 to 7, comprises a handle housing 64 and a piston 66, both having proximal and distal ends. In this embodiment, this piston 66 moves both longitudinally and rotatably with respect to the handle housing 64. The housing 64 and piston 66 preferably both comprise a rigid plastic, such as Delrin®, an acetal homopolymer commercially available from DuPont. The proximal end of the piston 66 is slidably and rotatably mounted within a piston chamber in the distal end of the handle housing 64. The distal end of the piston 66 is fixedly attached to the proximal end of the catheter body 12. The piston 66 has a thumb control 68 at its distal end.

In the depicted embodiment, the handle housing 64 comprises a proximal section 130 and a distal section 132. The distal end of the proximal section 130 of the housing 64 comprises a circumferential notch 134 into which the proximal end of the distal section 132 fits. The proximal section 130 and the distal section 132 can be press-fit together. If desired, the handle housing 64 can be formed of a single piece of plastic instead of proximal and distal sections. Around the distal section 132 of the handle housing 64 is provided a grip piece 136 made of rubber or the like to provide comfort to the user.

As shown in FIG. 6, the piston has first and second longitudinal grooves 70 and 72, each of the grooves having a proximal and distal end. The distal ends of the longitudinal grooves 70 and 72 are connected by a circumferential groove 74. The longitudinal grooves 70 and 72 are deeper than the circumferential groove 74, creating a step 78 at the distal ends of the longitudinal grooves under the circumferential groove.

A puller wire anchor 76 is slidably mounted within each longitudinal groove 70 and 72. The two puller wire anchors 76 each comprise a short metal rod, preferably made of aluminum or stainless steel. The step 78 at the distal ends of the longitudinal grooves 70 and 72 prevents the puller wire anchors 76 from sliding into the circumferential groove 74.

The proximal end of each puller wire 50 is fixedly attached to a corresponding puller wire anchor 76 by any suitable means, for example, by soldering the puller wire into a hole in the metal rod. Alternatively, the rod can have a small hole at its distal end and a larger hole at its proximal end. Preferably, a piece of hypodermic stock or the like is crimped on the proximal end of the puller wire. The hypodermic stock fits into the larger hole in the rod, but not the smaller hole, preventing the puller wire from being pulled distally out of the rod.

An internal passage 77 extends within the piston 66 through which the puller wires 50 and lead wires (not shown) extend. Two generally diagonally small holes 80 are provided in the step 78, each in general alignment with one of the longitudinal grooves 70 and 72 and in communication with the internal passage 77. The puller wires 50 extend through the holes 80 for connection to the puller wire anchors 76.

A set screw 82 extends radially inwardly from the handle housing 64 into the circumferential groove 74. When the piston 66 and housing 64 are in the positions shown in FIG. 7, the piston can be rotated between first and second positions relative to the housing. Rotation of the piston 66 relative to the housing 64 results in movement of the circumferential groove 74 relative to the set screw 82. When the piston 66 is in its first position, the set screw 82 is aligned with the first longitudinal groove 70, as shown in FIG. 7. When the piston 66 is in its second position, the set screw 82 is aligned with the second longitudinal groove 72. As would be recognized by one skilled in the art, the set screw 82 could be replaced by a pin, ring or the like (for example, as described below) that is held stationary relative to the piston 66, whether or not fixedly attached to the handle housing 64.

Distal movement of the piston 66 relative to the handle housing 64 results in longitudinal movement of the piston relative to the stationary set screw 82. When the set screw 82 is in its first position (i.e., aligned with the first longitudinal groove 70) and the piston 66 is moved distally relative to the handle housing 64, the first longitudinal groove 70 (along with the piston) slides distally relative to the set screw, which extends radially inwardly into the first longitudinal groove. However, distal movement of the puller wire anchor 76a in the first longitudinal groove 70 is blocked by the stationary set screw 82. Hence, the puller wire 50 connected to the blocked puller wire anchor 76a is also held stationary relative to the distally moving piston 66 and catheter body 12, which is fixedly attached to the piston. This results in deflection of the tip section 14 in the direction of the off-axis lumen 28 or 30 into which that puller wire 50 extends.

Similarly, when the set screw 82 is in its second position (i.e., aligned with the second longitudinal groove 72) and the piston 66 is moved distally relative to the handle housing 64 and set screw, the set screw 82 blocks movement of the puller wire anchor 76b, which remains stationary relative to the distally-moving piston. The puller wire 50 connected to the puller wire anchor 76b is held stationary relative to the distally moving piston 66 and catheter body 12, thus deflecting the tip section 14 in the direction of the off-axis lumen 28 or 30 into which that puller wire extends.

This design permits deflection of the tip section 14 to form two different curves, and preferably to deflect in two different directions, while preventing simultaneous movement of the puller wires 50.

As would be recognized to one skilled in the art, the above-described design could be used with a unidirectional catheter, i.e., having only a single puller wire. If only a single puller wire is included in the catheter, only a single longitudinal groove is provided in the piston. A circumferential groove is not necessary, but the set screw (or other pin) must extend into the longitudinal groove distal the puller wire anchor.

An alternative embodiment of the inventive control handle 16 is shown in FIGS. 8 to 13. The handle 16 comprises a handle housing 64 and a piston assembly 65, both having proximal and distal ends. The piston assembly 65 comprises a piston 66 at its proximal end and a thumb control 68 at its distal end, as well as additional components described in more detail below. The proximal end of the piston assembly 65 is slidably mounted within a piston chamber in the distal end of the handle housing 64. The distal end of the piston assembly 65 is fixedly attached to the proximal end of the catheter body 12. The piston 66 comprises an internal passage 77 extending therethrough through which the puller wires 50 and lead wires (not shown) extend.

The handle housing 64 comprises a proximal section 130 and a distal section 132. The distal end of the proximal section 130 of the housing 64 comprises a circumferential notch 134 into which the proximal end of the distal section 132 fits. The proximal section 130 and the distal section 132 can be press-fit together. Around the distal section 132 of the handle housing 64 is provided a grip piece 136 made of rubber or the like to provide comfort to the user.

The piston chamber has a first inner diameter 138, a second inner diameter 140, and a third inner diameter 142. The first inner diameter 138 is proximal the second inner diameter 140, both of which are distal the third inner diameter 142. The second inner diameter 140 is smaller than the first inner diameter 138, but is only slightly larger than the outer diameter of the piston 66. The third inner diameter 142 is smaller than the first inner diameter 138 and preferably similar in size to the second inner diameter 140.

Figure 11:
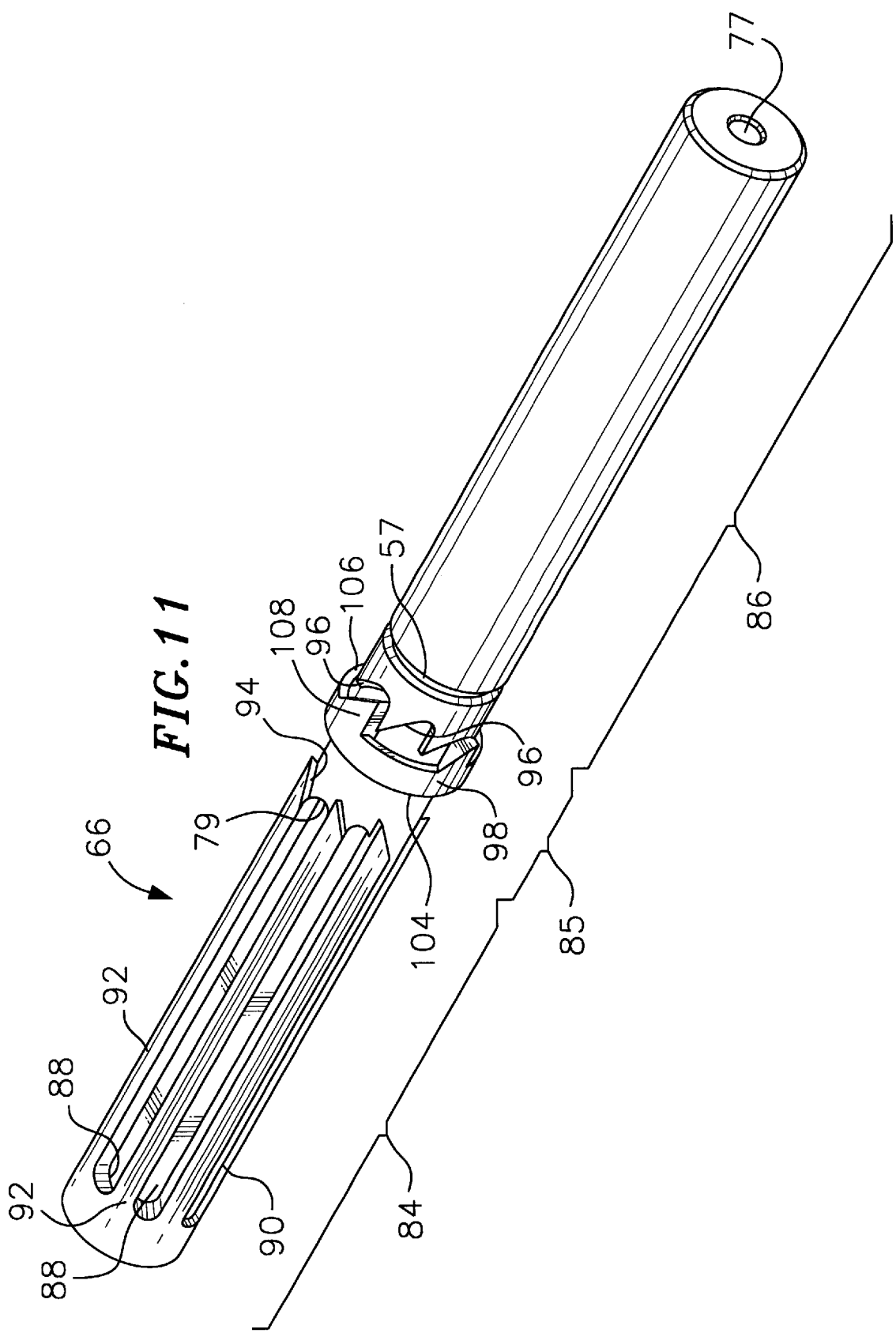
FIG. 11 is a perspective view of the proximal end of the piston of the handle of FIGS. 8 to 10.

FIG. 11 shows the proximal portion of the piston assembly 65, which comprises a proximal section 84, a distal section 86, and a circumferential recess 85 between the proximal section and distal section. The proximal section 84 comprises a series of longitudinal grooves, including deep longitudinal grooves 88 and shallow longitudinal grooves 90, about its entire circumference. The depicted embodiment has two deep longitudinal grooves 88 and four shallow longitudinal grooves 90, as shown best in FIG. 13. The two deep longitudinal grooves 88 are adjacent to each other. The longitudinal grooves 88 and 90 are separated from one another by dividing walls 92. Each dividing wall 92 has an angled distal end 94.

A puller wire anchor 76 is slidably disposed within each deep longitudinal groove 88. The distal ends of the deep longitudinal grooves 88 terminate in a vertical wall 79. Each vertical wall 79 contains a small hole (not shown). Two puller wires 50 extend through the internal passage 77 and through one of the small holes so that the puller wires can be attached to the puller wire anchors 76 as described above.

The distal section 86, which has proximal and distal ends, is spaced apart from the proximal section 84 by the circumferential recess 85. The proximal end of the distal section 86 comprises a plurality of tooth-shaped notches 96. Preferably the number of tooth-shaped notches 96 is the same as the number of dividing walls 92, which in the depicted embodiment is six.

The piston assembly 65 further comprises a ring 98 rotatably mounted on the piston 66. The ring 98 is preferably made of a generally rigid plastic, such as Delrin®, acrylonitrile-butadiene-styrene resin, polyester, polyethylene or the like. The ring 98 has a proximal end 104 and a distal end 106. The outer diameter of the ring 98 is slightly greater than the outer diameter of the distal portion of the piston 66. The inner diameter of the ring 98 is slightly greater than the outer diameter of the circumferential recess 85.

Figure 12:
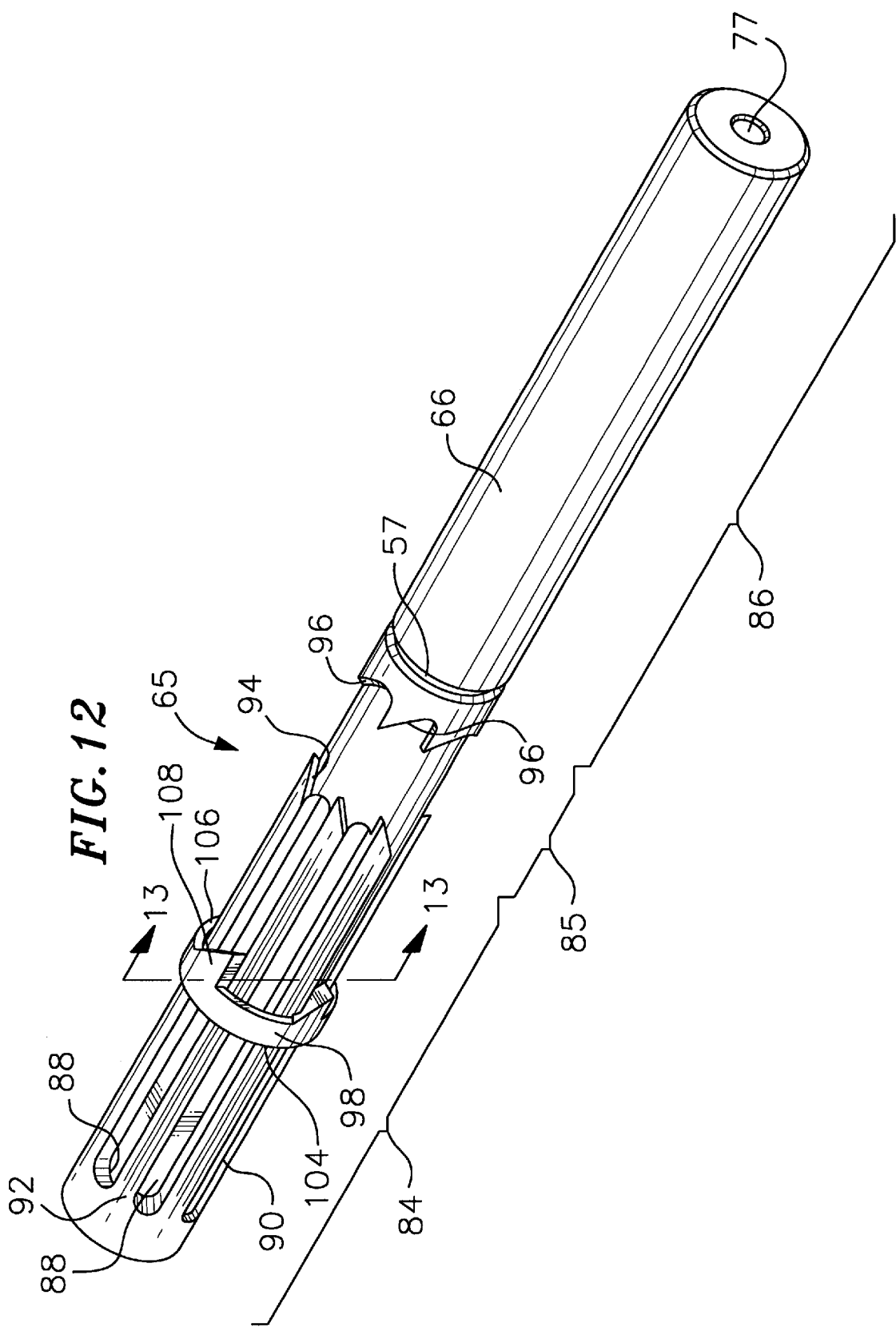
FIG. 12 is a perspective view of the proximal end of the piston of FIG. 11 wherein the ring has been slid proximally along the length of the piston.
Figure 13:
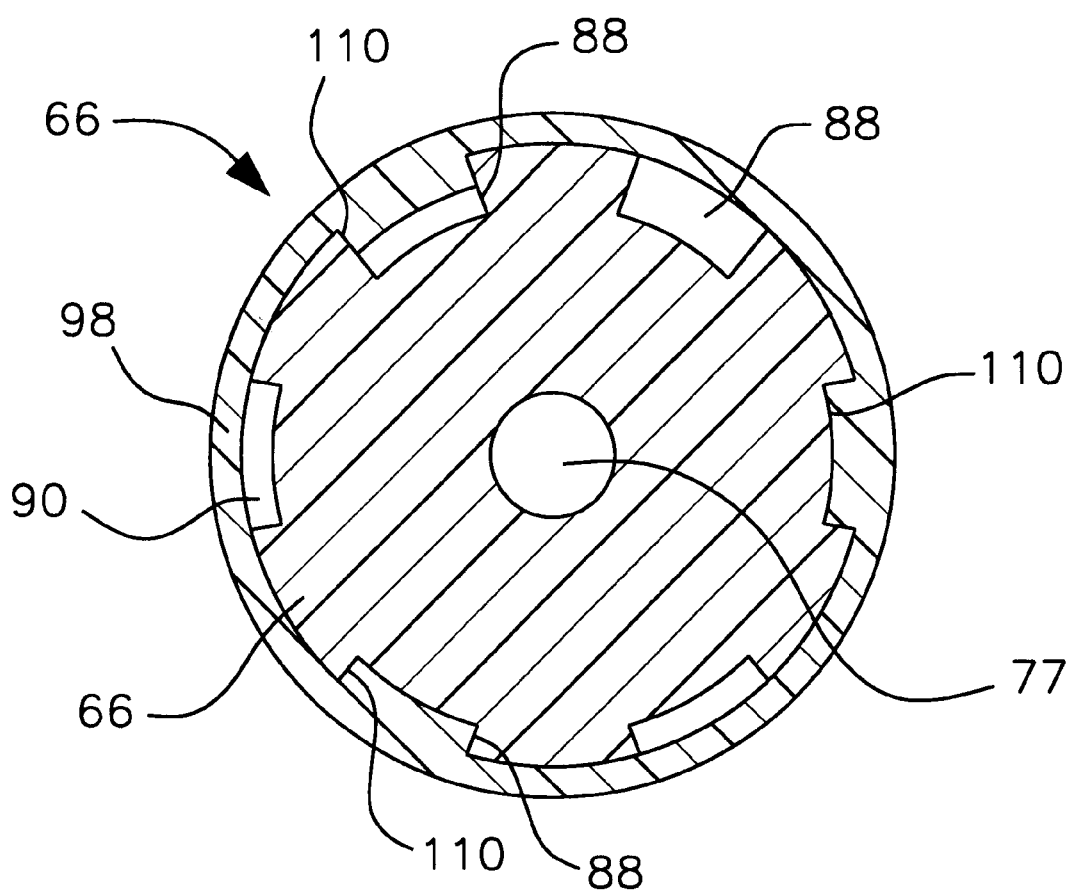
FIG. 13 is an end cross-sectional view of the piston of FIG. 12 along line 13—13.

The ring 98 has a plurality of projections 110 that extend radially inwardly into the circumferential recess 85 and that are sized to be received by the longitudinal grooves 88 and 90. FIG. 12 depicts the ring 98 slid proximally so that it is positioned over the longitudinal grooves 88 and 90 with the projections 110 extending inwardly into the grooves. As can be seen from FIG. 13, the projections 110 are spaced apart so that they can be aligned with every other longitudinal groove 88 and 90. In the depicted embodiment, three projections 110 are provided on the ring 98.

The distal end 106 of the ring 98 comprises a plurality of teeth 108 spaced apart to be aligned with every other notch 96. Accordingly, the number of teeth 108 is equal to half the number of notches 96. In the depicted embodiment, the ring 98 contains three teeth 108. The teeth 108 have a thickness so they project inward, preferably to about the same depth as the projections 110.

Figure 10:
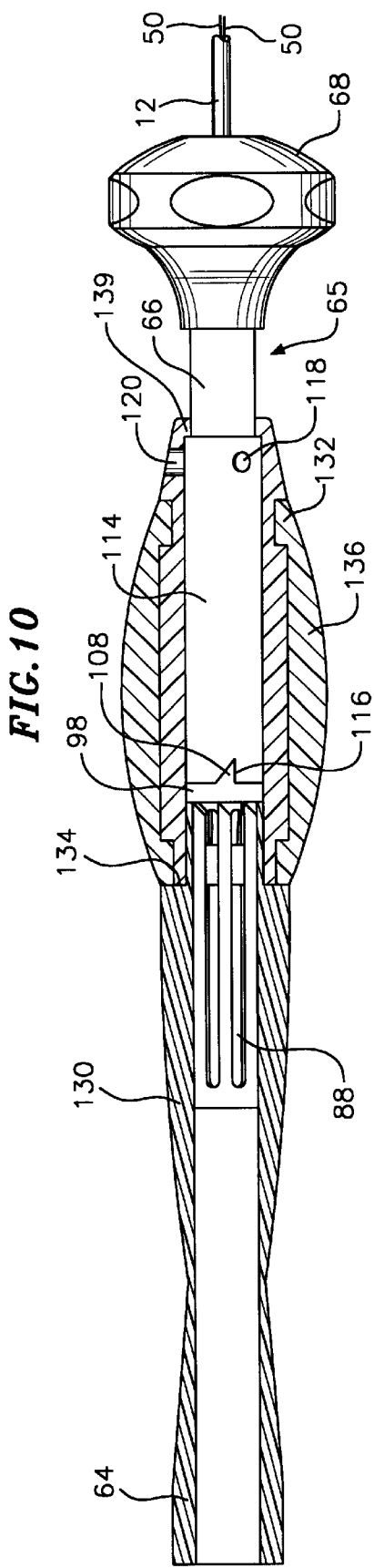
FIG. 10 is a side cross partial cross-sectional view of the handle of FIG. 8 with the sleeve wherein only the handle housing is shown in cross section.

As shown in FIG. 10, the piston assembly 65 further comprises a cylindrical sleeve 114 disposed about the distal section 86 of the piston 66. The sleeve 114, which has proximal and distal ends, is preferably made of a generally rigid plastic, such as Delrin®, polycarbonate or the like. The proximal end of the sleeve 114 contains three tooth-shaped notches 116 around its circumference that generally correspond in size, shape and position to the three teeth 108 on the distal end 106 of the ring 98. Thus, the proximal end of the sleeve 114 fits against the top or outer portion of the ring 98, and the projections 110 on the ring fit against the notches 96 on the proximal end of the distal section 86 of the piston.

If the number of teeth 108 on the ring 98 is increased or decreased, the number of tooth-shaped notches 116 on the sleeve 114 is correspondingly increased or decreased. The ring 98 and sleeve 114 rotate together about the piston 66 due to the interlocking between the tooth-shaped notches 116 on the sleeve and the teeth 108 on the ring. Preferably, the piston 66 comprises a circumferential groove 57 into which an o-ring (not shown) fits to seal the space between the piston and the sleeve.

The ring 98 and sleeve 114 have approximately the same outer diameter, which is smaller than the first inner diameter 138 of the piston chamber but larger than the second and third diameters 140 and 142 of the piston chamber. Due to the difference between the first inner diameter 138 and the second inner diameter 140, the handle housing 64 comprises a distal cylindrical flange 139 at the distal end of the piston chamber to prevent distal movement of the sleeve 114 (and thus the ring 98) relative to the housing, which also prevents distal movement of the sleeve out of the piston chamber. Due to the difference between the first inner diameter 138 and the third inner diameter 142, the handle housing 64 comprises a proximal cylindrical flange 141 midway through the piston chamber to prevent proximal movement of the ring 98 (and thus the sleeve 114) relative to the housing.

Movement of the piston 66 distally relative to the handle housing 64, e.g., by pushing on the thumb rest 68, results in the piston sliding distally relative to the sleeve 114 and ring 98 so that the ring is positioned over the longitudinal grooves 88 and 90 rather than the circumferential recess 85, as shown in FIG. 12. As the piston 66 moves distally, the projections 110 on the ring 98 are received by every other of the longitudinal grooves 88 and 90. In the arrangement described, one projection 110 will be received by one of the deep longitudinal grooves 88, but not the other. As the piston 66 moves distally relative to the ring 98, the projection 110 extending into the deep longitudinal groove 88 engages and blocks the puller wire anchor 76 in that groove, holding it and its associated puller wire 50 stationary relative to the distally-moving piston 66. Such movement results in deflection of the tip section 14 in the direction of the off-axis lumen into which the distal end of the puller wire 50 extends. As would be recognized by one skilled in the art, the ring 98 can be engaged by the handle housing 64 in any other manner such that the distal or proximal movement of the piston 66 relative to the housing causes the ring to remain longitudinally stationary relative to the distally or proximally moving piston, but still rotatable on the piston.

To engage the puller wire anchor 76b in the adjacent deep longitudinal groove 88, and thus enable deflection of the tip section in the direction of the off-axis lumen of the other puller wire 50, the projections 110 must be moved into alignment with the adjacent longitudinal grooves. To accomplish this, the piston 66 is moved proximally relative to the handle housing 64 until the teeth 108 on the ring 98 engage the tooth shaped notches 96 on the proximal end of the distal section of the piston 86. Because of the shapes of the teeth 108 and the notches 96, the ring 98 rotates as the teeth 108 engage the notches 96. The amount of rotation results in the projections 110 on the ring 98 being aligned with the adjacent longitudinal grooves 88.

As the piston 64 is again moved distally relative to the handle housing 64 and ring 98, the projections 110 are received by the adjacent longitudinal grooves 88 and 90. The projection 110 received by the deep longitudinal groove 88 engages and blocks distal movement of the puller wire anchor 76b in that groove, holding it stationary relative to the distally-moving piston 66 in a manner similar to that described above. This also holds the puller wire 50 anchored to that puller wire anchor 76b stationary relative to the distally-moving piston 66 and catheter body 12, resulting in deflection of the tip section 14 in the direction of the off-axis lumen into which that puller wire extends.

When it is desired to again deflect the tip section 14 in the direction of the puller wire 50 in the first deep longitudinal groove 88, the piston 66 is again moved proximally until the teeth 108 on the ring 98 engage the tooth shaped notches 96. The ring 98 again rotates relative to the piston 66 as the teeth 108 of the ring engage the notches 96. A different projection 110 then comes into alignment with the first deep longitudinal groove 88.

In a particularly preferred embodiment, an identification mechanism is provided so that the physician can readily ascertain which puller wire 50 is engaged. A preferred mechanism comprises three holes 118 spaced 120° apart around the circumference of the sleeve 114 near its distal end, as shown in FIG. 10. The sleeve 114 is a different color than the piston 66. The distal section 132 of the handle housing 64 has a hole 120 generally positioned in line with the holes 118 so that one of the holes 118 can be aligned with the hole 120. As the sleeve 114 rotates relative to the piston 66 and housing 64, it is positioned in one of six positions relative to the piston and housing. In three of those positions, one of the holes 118 is aligned with the hole 120 so that the user can see the piston 66 through the hole 120. These three positions correspond to one of the puller wires being blocked. In the other three positions, which correspond to the other puller wire being blocked, the user sees the sleeve 114 through the hole 120. By this design, the user can determine which puller wire is blocked, and thus how the tip section will deflect, by seeing either the color of the sleeve or the color of the piston through the hole 120 in the handle housing.

If desired, a set screw (not shown) can be provided to assure that the piston 66 is not separated from the handle housing 64. For example, the set screw could extend through the handle housing 64 and into one of the shallow longitudinal grooves 90 of the piston 66. Other means for assuring that the piston is not separated from the handle housing can also be used.

As would be recognized by one skilled in the art, the ring 98 and sleeve 114 could be replaced with a single piece that performs all of the functions of the ring and sleeve described above. Alternatively, the sleeve 114 could be removed altogether. With such a design, the length of the distal section 130 of the handle housing 64 having the first inner diameter 138 would be decreased so that the second inner diameter 140 is much closer to the ring 98.

Additionally, the above-described handle designs can be used with a multidirectional catheter having more than two puller wires. In the design of FIGS. 5 to 7, the number of longitudinal grooves (and puller wire anchors) would be increased to correspond to the number of puller wires. In the design of FIGS. 8 to 13, the number of deep longitudinal grooves (and puller wire anchors) would be increased to correspond to the number of puller wires. To prevent simultaneous movement of the tip section in the directions of two different puller wires, the number of protrusions on the ring would be modified so that only one protrusion extends into one of the deep longitudinal grooves. Thus, for example, if three puller wires are used, the protrusions on the ring would be aligned with every third longitudinal groove. If four puller wires are used, the piston would be modified to have four deep longitudinal grooves and four shallow longitudinal grooves, and the protrusions on the ring would be aligned with every fourth longitudinal groove.

It may also be desirable to permit simultaneous movement of two or more puller wires, for example, to permit curvature of the tip section in two directions simultaneously, for example, as disclosed in U.S. patent application Ser. No. 08/924,611, entitled "Omni-Directional Steerable Catheter", the disclosure of which is incorporated herein by reference. Other similar modifications would be obvious to one skilled in the art.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the deep longitudinal grooves need not be adjacent each other. Alternatively, all of the longitudinal grooves can be of the same depth, similar to the deep longitudinal grooves. Additionally the ring can contain more or less teeth as desired, but preferably a number equal to the number of protrusions on the ring for simplicity in manufacturing the ring.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A steerable catheter comprising:

a catheter body having a tubular wall, proximal and distal ends, and at least one lumen extending therethrough;

a tip section comprising a flexible tubing having proximal and distal ends and at least one lumen extending therethrough, the proximal end of the tip section being fixedly attached to the distal end of the catheter body;

a control handle mounted at its distal end to the proximal end of the catheter body comprising:

a housing having proximal and distal ends and a piston chamber;

a piston having proximal and distal ends slidably mounted in the piston chamber of the housing, the distal end of the piston being fixedly attached to the proximal end of the catheter body, said piston being longitudinally movable relative to the housing between proximal and distal positions, said piston comprising a longitudinal groove having proximal and distal ends and extending along a portion of the length of the piston;

a puller wire anchor slidably disposed within the longitudinal groove;

a puller wire having proximal and distal ends extending from the control handle, through a lumen in the catheter body and into a lumen in the tip section, the proximal end of the puller wire being fixedly attached to the puller wire anchor in the control handle, means attached to the distal end of the puller wire for deflecting the tip section in a select direction in response to distal movement of the piston and catheter body relative to the puller wire anchor; and means for preventing distal movement of the puller wire anchor within the groove when the piston is moved distally.

2. A catheter according to claim 1, wherein the means for deflecting the tip section comprises an off-axis lumen in the tip section into which the puller wire extends and an anchor that anchors the puller wire to the tip section.

3. A catheter according to claim 1, further comprising a tip electrode.

4. A catheter according to claim 3, wherein the means for deflecting the tip section comprises an off-axis lumen in the tip section into which the puller wire extends and means for fixedly attaching the puller wire to the tip electrode.

5. A catheter according to claim 1, wherein the handle further comprises an internal passage extending within the piston and a hole connecting the internal passage to the longitudinal groove, whereby the puller wire passes through the internal passage and hole and into the longitudinal groove.

6. A catheter according to claim 1, wherein the handle further comprises a thumb control at the distal end of the piston.

7. A catheter according to claim 1, wherein the preventing means comprises a set screw fixedly attached to the inner surface of the handle housing that extends radially inwardly.

8. A multidirectional steerable catheter comprising:
a catheter body having a tubular wall, proximal and distal ends, and at least one lumen extending therethrough;
a tip section comprising a flexible tubing having proximal and distal ends and at least one lumen extending therethrough, the proximal end of the tip section being fixedly attached to the distal end of the catheter body;
a control handle mounted at its distal end to the proximal end of the catheter body comprising:
  a housing having proximal and distal ends and a piston chamber;
  a piston having proximal and distal ends slidably and rotatably mounted in the piston chamber of the housing, the distal end of the piston body fixedly attached to the proximal end of the catheter body, said piston being longitudinally movable relative to the housing between proximal and distal positions and rotatably movable relative to the housing between first and second positions, said piston comprising at least two longitudinal grooves having proximal and distal ends and extending along a portion of the length of the piston and a circumferential groove connecting the distal ends of the longitudinal grooves;
  first and second puller wire anchors, each puller wire anchor slidably disposed within a corresponding longitudinal groove;
  first and second puller wires having proximal and distal ends, each puller wire extending from the control handle, through a lumen in the catheter body and into a lumen in the tip section, the proximal end of each puller wire being fixedly attached to a separate puller wire anchor in the control handle;
  first means attached to the distal end of the first puller wire for deflecting the tip section to form a first curve in response to distal movement of the piston and catheter body relative to the first puller wire and puller wire anchor;
  second means attached to the distal end of the second puller wire for deflecting the tip section to form a second curve different from the first curve in response to distal movement of the piston and catheter body relative to the second puller wire and puller wire anchor;
  means for selectively preventing distal movement of one of the first and second puller wire anchors when the piston is moved distally.

9. A catheter according to claim 8, wherein the first and second means for causing deflection of the tip section comprise first and second off-axis lumens in the tip section into which the first and second puller wires extend and anchors that anchor the puller wires to the tip section.

10. A catheter according to claim 8 further comprising a tip electrode.

11. A catheter according to claim 10, wherein the means for causing deflection of the tip section comprises first and second off-axis lumens in the tip section into which the first and second puller wires extend and means for fixedly attaching at least one puller wire to the tip electrode.

12. A catheter according to claim 8, wherein the handle further comprises an internal passage extending within the piston and first and second holes connecting the internal passage to the first and second longitudinal groove, whereby the first puller wire passes through the internal passage and first hole and into the first longitudinal groove, and the second puller wire passes through the internal passage and second hole and into the second longitudinal groove.

13. A catheter according to claim 8, further comprising means for preventing the first and second puller wire anchors from passing into the circumferential groove.

14. A catheter according to claim 13, wherein the means for preventing the first and second puller wire anchors from passing into the circumferential groove comprises steps at the distal ends of the longitudinal grooves.

15. A catheter according to claim 8, wherein the handle further comprises a thumb control at the distal end of the piston.

16. A catheter according to claim 8, wherein the preventing means comprises a set screw fixedly attached to the inner surface of the handle housing that extends radially inwardly.

17. A catheter according to claim 8 comprising more than two puller wires and more than two puller wire anchors.

18. A catheter according to claim 8, comprising two puller wires that extend into opposing off-axis lumens in the tip section.

* * * * *